United States Patent [19]

Pei et al.

[11] Patent Number: 5,571,929
[45] Date of Patent: Nov. 5, 1996

[54] RESOLUTION AND REDUCTION OF PHYSOSTIGMINE INTERMEDIATES AND DERIVATIVES

[75] Inventors: Xue F. Pei, Washington, D.C.; Arnold Brossi, Bethesda, Md.

[73] Assignee: The United States of America as represented by the Department of Health and Human Services, Washington, D.C.

[21] Appl. No.: 350,819

[22] Filed: Dec. 7, 1994

[51] Int. Cl.[6] ................................................ C07D 209/34
[52] U.S. Cl. .................................................. 548/486
[58] Field of Search .............................................. 548/486

[56] References Cited

U.S. PATENT DOCUMENTS 4,164,583  8/1979  Achini et al. .
4,529,736  9/1985  McKenzie et al. .
4,791,107 12/1988  Hamer et al. .
4,900,748  2/1990  Brossi et al. .

OTHER PUBLICATIONS

Atack et al., J. Pharm & Exp. Ther., 249, pp. 194–202 (1989).
Julian et al., J. Am. Chem. Soc., 57, 563–566 (1935).
Julian et al., J. Am. Chem. Soc., 57, 755–757 (1935).
Kobayashi, Liebigs Ann. Chem., 536, 143–162 (1935).
Dale et al., J. Pharm. Pharmac., 22, 889–896 (1970).
Schönenberger et al., Helvetica Chimica Acta, 69, 1486–1497 (1986).
Yu et al., Heterocycles, 27, (3), 745–750 (1988).
Yu et al., Heterocycles, 27, (7), 1709–1712 (1988).
Pei et al., Helvetica Chimica Acta, 77, 1412–1422 (1994).
Lee et al., J. Org. Chem., 56, 872–875 (1991).
Pallavicini et al., Tetrahedron:Asymmetry, 5, (1), 111–116 (1994).
Yu et al., Heterocycles, 36, (6), 1279–1285 (1993).
Luo et al., Heterocycles, 31, (2), 283–287 (1990).
Yu et al., Heterocycles, 36, (8), 1791–1794 (1993).
Schönenberger et al., J. Med. Chem., 2268–2273 (1986).
Brzostowska et al., Med. Chem. Res., 2, 238–246 (1992).
Yu et al., J. Med. Chem., 31, 2297–2300 (1988).
Lee et al., J. Chrom., 523, 317–320 (1990).
Takano et al., The Alkaloids, 36, 225–251 (1989).
Francotte et al., J. Chrom., 576, 1–45 (1992).
Pallavicini et al., "New Asymmetric Synthesis of (–)-Esermethole", Tetrahedron, 5(3), 363 370 (1994).
Robinson et al., "Alkaloids of Physostigma Venenosum", J. Chem. Soc., 3336–3339 (1965).

*Primary Examiner*—Jacqueline Haley
*Attorney, Agent, or Firm*—Leydig, Voit & Mayer, Ltd.

[57] ABSTRACT

One aspect of the present invention provides for the separation of a racemic mixture or a mixture enriched with one or other enantiomer, said mixture comprising the enantiomers of the compound of the formula:

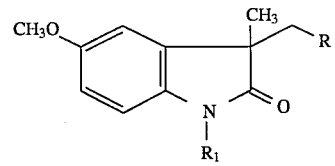

wherein R is CN or CONHR' where R' is a $C_1$–$C_6$ alkyl, hydrogen, or benzyl, and $R_1$ is $C_1$–$C_6$ alkyl or benzyl. Another aspect of the present invention provides a method of preparing a compound of the formula:

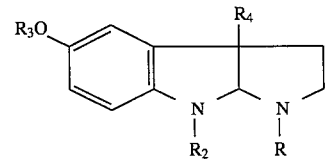

wherein R is H, $C_1$–$C_6$ alkyl or benzyl, and wherein $R_2$, $R_3$, and $R_4$ are $C_1$–$C_6$ alkyl or benzyl.

29 Claims, No Drawings

RESOLUTION AND REDUCTION OF PHYSOSTIGMINE INTERMEDIATES AND DERIVATIVES

TECHNICAL FIELD OF THE INVENTION

The present invention generally relates to methods for preparing physostigmine derivatives, as well as to the separation of racemic mixtures obtained during their preparation.

BACKGROUND OF THE INVENTION

Physostigmine, represented by the formula I below,

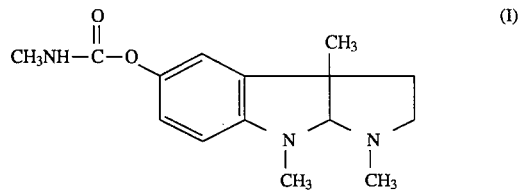

is a naturally-occurring, optically-active compound which has shown encouraging responses in treating Alzheimer's disease, due to its anticholinesterase activity. However, as in the case of many pharmaceuticals, one of the enantiomers of this compound i.e., the (3aS) enantiomer, demonstrates significantly greater efficacy as compared to the other.

The (3aS) enantiomer of physostigmine is presently extracted from Calabar beans, which are of West African origin. However, the limited availability of these beans has resulted in a scarcity of physostigmine, and what little is available is relatively expensive. These factors have caused the pharmaceutical industry and academia to devise alternate routes to synthetically obtain the (3aS) enantiomer of physostigmine.

In order to synthesize the (3aS) enantiomer of physostigmine, it is necessary to provide an optically-pure intermediate, (3aS-cis)-esermethole (II).

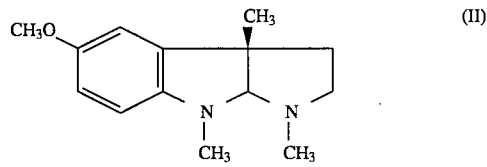

Methods for the preparation of this optically-pure intermediate are well known, e.g., Julian et al., *J. Am. Chem. Soc.*, 57, 563–566 (1935) ("Julian et al. I"); Julian et al., *J. Am. Chem. Soc.*, 57, 755–757 (1935) ("Julian et al. II"); Kobayashi, *Liebigs Ann. Chem.*, 536, 143 et seq. (1935); and Dale et al., *J. Pharm. Pharmacol.*, 22, 889–896 (1970). These methods comprise a synthesis in which 1,3-dimethoxy-5-ethoxy oxindole (III)

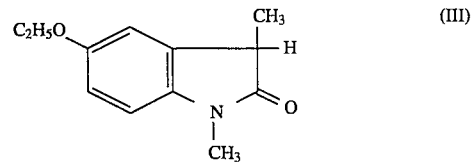

is 3-cyanoalkylated using chloroacetonitrile, with the resulting nitrile (IV)

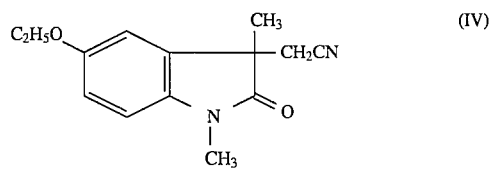

being reduced to a racemic mixture of the amine (V)

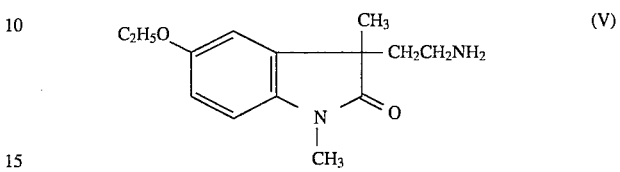

The racemic mixture is subsequently separated into its enantiomers by a chemical process. This chemical process requires that the racemic amine mixture be successively treated with camphorsulfonic acid and tartaric acid. Each acid functions to crystallize one of the enantiomers (the tartaric acid crystallizing the desirable (3aS) enantiomer), thereby providing for their separation. After separation, the desired (3aS) enantiomer is then cyclized using a reducing agent comprising sodium and ethanol.

Others have modified the foregoing method of cyanoalkylation so that the racemic amine mixture contains the (3aS) enantiomer in excess (about 73%). Lee et al., *J. Org. Chem.*, 56, 872–875 (1991) ("Lee et al. I"). The separation of this enantiomer from the racemic amine mixture, however, was also accomplished by treating the mixture with tartaric acid. Pallavicini et al., *Tetrahedron: Asymmetry*, 5, 111 et. seq. (1994).

While the foregoing separations of the (3aS) enantiomer using chemical methods, e.g., crystallization using tartaric acid, are operable, there are certain drawbacks to the use of such methods. One of these is the relatively low yields obtainable thereby, this being due to the several steps that are required to be executed to effect such separation. These methods may also employ the use of caustic chemicals.

Another separation method used to effect the separation of racemates which attempts to overcome the drawbacks associated with the aforesaid chemical separation methods involves the use of a separation column. These columns typically include a material therein, referred to as a stationary phase, which functions to cause each enantiomer of a racemic mixture to move through the column at a different rate. Thus, upon operation, when a mobile phase is passed through a column in which the racemic mixture in transiently entrained, one of the enantiomers will elute more rapidly than the other. This allows one to obtain optically-pure solutions of enantiomers by collecting the eluant at different times. This type of one-step separation process is not only easier to complete as compared to the aforementioned multi-step chemical separation processes, but also provides a relatively greater yield of the desired enantiomer.

Articles which relate to the analytical separation of certain physostigmine intermediates into their respective enantiomers using such a column include Lee et al. I and Lee et al., *J. Chromatography*, 523, 317–320 (1990) ("Lee et al. II"). Lee et al. II describes the use of relatively expensive columns (Chiracel OD/OJ) which contain a benzoylor carbamate-derivatized cellulose-coated stationary phase in the analysis of racemic mixtures, e.g., of (3aS) and (3aR) enantiomers of 1,3-dimethyl-3-cyanomethyl-5-methoxyoxindole (VI)

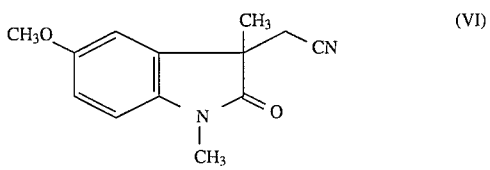

using isopropanol-hexane (10:90) as the mobile phase, wherein the (3aR) enantiomer is the first to elute out of the column.

The work reported in Lee et al. II provides an assay for the intermediates, as opposed to providing a preparative separation method. Moreover, the process disclosed in this article appears to be relatively unpredictable, and highly compound-specific, in that the carbamate (—$CH_2$—$CH_2$—NH—$COOCH_3$) and dinitrobenzoyl (—$CH_2$—$CH_2$—NH—CO—3,5—$(NO_2)_2$—Ph) amide intermediates disclosed therein are said to be separable in the column, but, surprisingly, the acetamide (—$CH_2$—$CH_2$—NH—$COCH_3$) and benzoylamide (—CH2—CH2—NH—CO—Ph) intermediates were not found to be separable thereby. Lee et al. I also discloses an analytical method directed to the assay of the optical purity of the cyanomethyl and the aminoethyl physostigmine intermediates, and of esermethole, using the aforementioned Chiracel columns.

Once one has obtained a physostigmine intermediate, e.g., 1,3-dimethyl-3-cyanomethyl-5-methoxyoxindole (VI), in optically-pure form, by any known process, its efficient conversion into the closed-ring structure of physostigmine and derivatives thereof is of great interest.

Several methods for effecting the conversion of the intermediate into the desired closed-ring structure have been used. One of these methods, disclosed in Julian et al. I and II, and U.S. Pat. No. 4,791,107 to Hamer et al., uses a two-step procedure for the preparation of the physostigmine closed-ring structure starting from (3aS) 1,3-dimethyl-3-cyanomethyl-5-ethoxyoxindole (IV). In the first step, the cyanomethyl group is reduced by palladium/hydrogen to the aminoethyl group, which is then reduced in the second step by sodium in ethanol to obtain the closed-ring structure. In the case of this starting material, a further step, i.e, methylation of the closed-ring thus formed, or alternatively methylation of the aminoethyl group, is required to obtain (3aS) physostigmine.

A second method, set forth in Yu et al., *Heterocycles*, 36 (6), 1279–1285 (1993); Yu et al., *Heterocycles*, 27 (7), 1709–1712 (1988); and Lee et al. II, comprises a one-step method for effecting the aforesaid cyclization. This method provides for the reduction of the cyanomethyl derivative in a single step using the reducing agent lithium aluminum hydride. This reducing agent, however, is very hazardous due its extreme flammability.

Therefore, a need exists for a relatively high efficiency, low cost, separation process which is able to separate racemic mixtures of a relatively wider variety of physostigmine intermediates and derivatives thereof as compared to existing separation methods. Of course, a process which operates more quickly than existing processes, and which is able to provide for such separation on a preparative (as opposed to analytic) scale, would also be of great interest.

A further need exists for a safe and efficient method of effecting cyclization of physostigmine intermediates and derivatives thereof.

These and other objects and advantages of the present invention, as well as additional inventive features, will be apparent from the description of the invention provided herein.

SUMMARY OF THE INVENTION

One aspect of the present invention provides for the separation of a racemic mixture or a mixture enriched with one or other enantiomer, said mixture comprising the enantiomers of the compound of the formula:

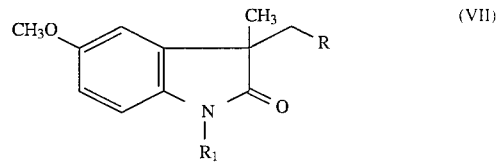

wherein R is CN or CONHR' where R' is a $C_1$—$C_6$ alkyl, hydrogen, or benzyl, and $R_1$ is $C_1$-$C_6$ alkyl or benzyl. The method comprises contacting the racemic mixture with a cellulosic solid phase material, eluting said mixture in contact with the solid phase material with an eluant comprising at least 50 vol. % $C_1$-$C_6$ alcohol, and recovering an eluted product having an enantiomeric excess greater than that of said mixture.

The method of the present invention provides a means by which the separation of a relatively broad range of physostigmine intermediates and derivatives thereof may be successfully completed. In addition to its relatively broad applicability, the method. provides excellent separation efficiencies—it provides products having a high level of optical purity (up to about 100% enantiomeric excess), at high yields. The method may further be completed faster than known separation methods, and is excellent for preparative synthesis. In addition, all of the foregoing advantages are achieved while using relatively inexpensive components, e.g., the method uses alcohol (e.g., at least 50 vol. %) in the mobile phase, which alcohol may be industrial grade.

Another aspect of the present invention provides a method of preparing a compound of the formula:

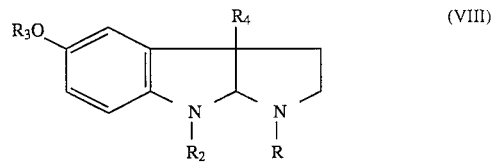

wherein R is H, $C_1$-$C_6$ alkyl, or benzyl, and wherein $R_2$, $R_3$, and $R_4$ are $C_1$-$C_6$ alkyl or benzyl. This method comprises contacting a compound of the formula:

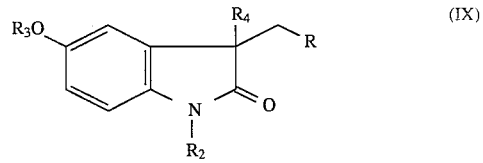

wherein R is CN or CONHR' where R' is a $C_1$-$C_6$ alkyl, hydrogen, or benzyl, and wherein $R_2$, $R_3$, and $R_4$ are $C_1$-$C_6$ alkyl or benzyl, with sodium dihydrido-bis(2-methoxyethoxy)-aluminate. This method provides a safe and efficient (single-step) method of effecting cyclization of physostigmine intermediates and derivatives thereof in that it does not require the use of lithium aluminum hydride, which is extremely flammable.

The invention may best be understood with reference to the following detailed description of the preferred embodiments.

DESCRIPTION OF THE PREFERRED EMBODIMENTS

One aspect of the present invention is a method which provides for the efficient separation of a relatively wide variety of physostigmine intermediates and derivatives thereof. Surprisingly, it was found that such separations could be effected in a more cost effective manner by using alcohol, and even industrial grade alcohol if desired, (as opposed to the relatively more expensive hexane which must be used in known methods) in the eluant in an amount of at least about 50 vol. %, and up to 100 vol. %, without any substantial loss in efficiency or yield. In fact, the method of the present invention provides further surprising results in that separations were able to be completed quicker, and, as mentioned previously, the method is able to separate a relatively broader range of physostigmine intermediates and derivatives, as compared to known methods, in both preparative and analytical separations.

The method of the present invention is able to separate from a racemic mixture or a mixture enriched with one or the other enantiomer of a physostigmine intermediate or derivative thereof, an enantiomer of the formula (VII) wherein R is CN or CONHR' where R' is a $C_1$–$C_6$ alkyl, hydrogen, or benzyl, and $R_1$ is $C_1$–$C_6$ alkyl or benzyl. The method comprises contacting that racemic mixture with a cellulosic solid phase material, eluting said mixture in contact with said material with an eluant comprising at least 50 vol. % $C_1$–$C_6$ alcohol, and recovering an eluted product having an enantiomeric excess greater than that of said mixture.

Advantageous results in separation efficiencies as compared to known separation processes have been obtained in respect to a certain group of the compounds of formula VII, e.g., wherein R is CN, $CONHCH_2C_6H_5$, or $CONHCH_3$, and $R_1$ is $CH_3$. These efficiencies include, but are not limited to, the time required to effect the separation, the separation yield, and material cost.

The amount of one enantiomer in a mixture of enantiomers, be it a product or starting mixture, is typically described in terms of enantiomeric excess ("ee"). The enantiomeric excess in regard to a particular enantiomer in relatively greater concentration ($ee_1$) may be calculated as follows:

$$ee_1 = (E_1 - E_2)/(E_1 + E_2) \times 100$$

wherein $E_1$ and $E_2$ are the weight (or moles) of the higher and lower concentration enantiomers, respectively. Advantageous results in the form of separation efficiencies, e.g., high optical purity levels in the product, have been observed when racemic mixtures possessing little or no enantiomeric excess as well as possessing enantiomeric excesses of from about 60–80% are separated in accordance with the method of the present invention.

When a separation is conducted in accordance with the present invention, the method provides the eluted product in an enantiomeric excess of at least about 80%∓5% preferably at least about 95–100% and most preferably substantially 100% (i.e., a substantially pure enantiomer).

The eluant used in the inventive method comprises at least 50 vol. % of an alcohol. The alcohol is advantageously an alkanol and, more advantageously, is selected from the group consisting of methanol, ethanol, propanol, isopropanol, n-butanol, sec-butanol, t-butanol, and mixtures thereof. Ethanol is preferably used alone as the alcohol component of the eluant because it provides the greatest separation efficiency compound to the pure methanol, although the precise reason for this is not fully understood at present.

The eluant may further comprise water. The inclusion of small amounts of water in the eluant, below about 10 vol. %, as is typically found in industrial grade alcohols, has been found to have no substantial deleterious effects upon the separation efficiencies. Therefore, one is able to use such relatively low cost industrial grade alcohols without a corresponding loss in separation efficiency.

Advantageously, then, the aqueous eluant may comprise at least about 70 vol. % of said alcohol, and preferably at least about 90 vol. % of said alcohol.

When methanol is used as the sole alcohol component in the eluant, however, the inclusion of water in the eluant, up to about 30 vol. %, actually improved certain of the separation efficiencies as compared to using only methanol as the eluant, e.g., the resolution factor and separation factor. The reasons for this phenomenon are not fully understood at present.

The solid phase material used in the separation of the present invention, which is typically packed within a chromatography column, may comprise any commercially available cellulosic material, i.e., any material which includes cellulose or a cellulose derivative. Advantageously, the cellulosic solid phase material is selected from the group consisting of cellulose triacetate, cellulose diacetate, cellulose p-methylbenzoate, cellulose 3,5-dimethylphenylcarbamate, and combinations thereof. These materials were found to provide products having high optical purity and yield in the context of the present invention.

The preferred cellulosic solid phase material is cellulose triacetate because it appears to interact with the alcohol-containing eluant in a manner which provides excellent separation properties, while being relatively inexpensive. The rationale underlying this interaction is unknown. The use of those two components in the method provides superior results, particularly when the eluant comprises 96 vol. % ethanol and 4 vol. % water.

While the cellulosic solid phase materials are available in a variety of forms, it is preferable to use micronized materials in the separations of the present invention. The particles which comprise those materials should preferably range from about 10 µm to about 40 µm in average diameter, and most preferably from about 15 µm to about 25 µm in average diameter. It was determined that such micronization of the cellulosic solid phase material provided optimal separation efficiencies in the inventive method. An example of the preferred cellulosic solid phase material is microcrystalline cellulose triacetate prepared by the heterogeneous acetylation of native microcrystalline cellulose. Microcrystalline cellulose triacetate is available from E. Merck of Darmstadt, Germany in a 15 µm to 25 µm particle size, and from Fluka Chemical Co. of Ronkonkoma, N.Y.

The present inventive method may be undertaken with the cellulosic solid phase material packed within any type of suitable chromatography column, including columns constructed of glass, stainless steel, or other inert material. The selection and preparation of an appropriate column which would be suitable to effect the separations of the present invention is well within the skill of an ordinary worker.

A second aspect of the present invention is a method for preparing a compound of the formula VIII, wherein wherein R is H, $C_1$–$C_6$ alkyl, or benzyl, and $R_2$, $R_3$, and $R_4$ are $C_1$–$C_6$ alkyl or benzyl. This method comprises contacting a compound of the formula (IX), wherein R is CN or CONHR' where R' is a $C_1$–$C_6$ alkyl, hydrogen, or benzyl, and wherein $R_2$, $R_3$, and $R_4$ are $C_1$–$C_6$ alkyl or benzyl, with a solution comprising sodium dihydrido-bis(2-methoxyethoxy)-aluminate. This method provides an efficient (single-step) method of effecting cyclization of the foregoing physostigmine intermediates and derivatives thereof, and, in addition, avoids the use of lithium aluminum hydride, an extremely flammable compound, as a reducing agent.

The method is particularly useful when one desires to cyclize certain physostigmine intermediates, e.g., those of formula (IX) wherein R is CN, CONHCH$_2$C$_6$H$_5$, or CONHCH$_3$, and R$_2$, R$_3$, and R$_4$ are CH$_3$. When R is CONHCH$_2$C$_6$H$_5$, the resulting compound has a benzyl group at the N$^1$ position. Since benzyl groups are known as good leaving groups, the cyclized compound having a benzyl group at the N$^1$ position provides a further advantage in that the benzyl group can be subsequently easily replaced by other desirable functional groups. For example, the benzyl group can be replaced by hydrogen by catalytic hydrogenation.

In the cyclization method of the present invention, the reducing agent is advantageously provided in an amount which is sufficient to effect the reductive cyclization of the total amount of the compound of formula (IX) which is present in the reaction mixture. This amount will typically range from about 0.5 mol % to about 2.0 mol %.

The aforesaid reductive cyclization is advantageously conducted while the reactive components are in solution. Most advantageously, the solution may comprise an inert solvent, the selection of such inert solvents being well within the skill of the ordinary worker. Examples of preferred solvents include benzene, toluene, xylene, and cyclohexane.

During the reductive cyclization, it is preferred that such be conducted in an inert atmosphere, most preferably in a nitrogen, argon, or helium atmosphere. If oxygen and/or moisture is present during the cyclization, destruction of the reducing agent can occur.

The reductive cyclization may be carried out at any suitable temperature, although improved yields are obtained when the reaction mixture has a temperature of between about 0° C. to about 60° C. Optimal results are obtained when the temperature of the mixture is maintained at ambient temperatures, e.g., about 20°–25° C.

The reaction should generally be left to proceed to completion, which may range in duration from about fifteen minutes to about 6 hours. Advantageously, substantial completion may be obtained within about 3 hours after the initiation of the reductive cyclization.

The following examples further illustrate the present invention but, of course, should not be construed as in any way limiting its scope.

The formulas of some of the compounds described in the illustrative examples are set forth below.

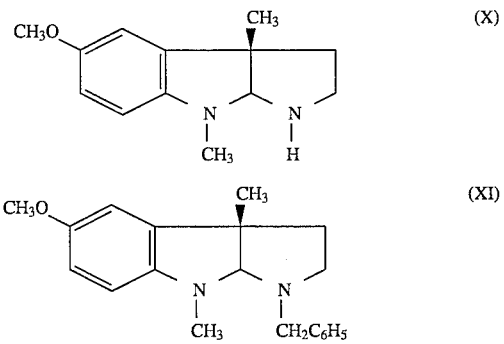

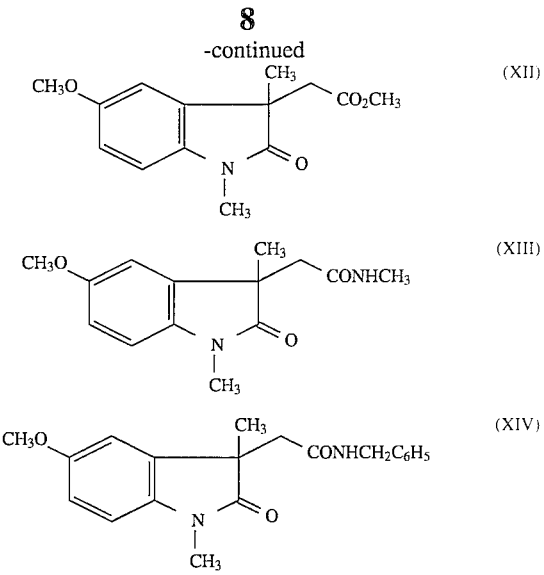

Further, all of the isolated enantiomers in the examples are at 100% ee.

EXAMPLE 1

A glass column (65 cm×2.5 cm ID) was slurry packed with 80 g of the solid phase material, cellulose triacetate, which had been pre-swollen in 200 ml of 95% ethanol solvent at 75° C. for 20 min. After removing the excess solvent, the solid phase material was washed by pumping through it 200 ml of 95% ethanol at a flow rate 0.5 ml/min.

166 mg of the racemic 1,3-dimethyl-3-cyanomethyl-5-methoxyoxindole (VI) was dissolved in 0.5 mL of the ethanol solvent and injected into the packed column. The mobile phase eluant was 95% ethanol and pumped at a flow rate of 0.5 ml/min. 3 ml fractions of the eluant eluting from the column were collected. Optical purity of the various fractions were checked by HPLC using a Chiracel OD column (25 cm×0.46 cm ID), hexane/isopropanol (80/20) as the mobile phase at a flow rate of 1.0 ml/min, and a UV detector.

The 3aR enantiomer eluted first. Fractions having pure enantiomers were combined separately, and the pure enantiomers were recovered after evaporation of solvent under reduced pressure. 81 mg of the 3aR enantiomer was obtained as colorless gum: $[\alpha]_D$ –50.5° (c=0.54, CHCl$_3$) in 49% yield. 80 mg of the 3aS enantiomer was obtained as colorless gum, $[\alpha]_D$ +50.6° (c=0.74, CHCl$_3$) in 48% yield. Certain fractions had enantiomeric mixtures. But the amounts of enantiomers present in these fractions were relatively small. These fractions were combined, and the solvent was evaporated to obtain 3.5 mg of mixture as a colorless gum. An analysis of all three products using a TLC plate (silica gel, CH$_2$Cl$_2$ with 2% MeOH) confirmed that the enantiomers were not damaged by the separation process.

EXAMPLE 2

270 mg of an optically active nitrile (VI) having a 64% ee of the 3aS enantiomer prepared by the asymmetric cyanoalkylation procedure reported in Lee et al. I was separated on the same column and under the same conditions as in Example 1 to obtain 40 mg of the 3aR enantiomer, which eluted first, as a colorless gum: $[\alpha]_D$ –50.5° (c=0.54, CHCl$_3$) in 15% yield, and 215 mg of the 3aS enantiomer as a colorless gum: $[\alpha]_D$ +50.6° (c=0.74, CHCl$_3$) in 80% yield, and 15 mg of mixture as a colorless gum. An analysis of all three products using TLC plate (silica gel, CH$_2$Cl$_2$ with 2% MeOH) and infrared and NMR spectral data, confirmed that the enantiomers were not damaged by the process.

EXAMPLE 3

160 mg of the 3aS enantiomer of the nitrile (VI) prepared as in Example 1 was dissolved in 5 ml of toluene, and 0.4 ml of a 70% toluene solution of sodium dihydrido bis-(2-methoxyethoxy)-aluminate (Vitride) was added. The mixture was stirred at ambient temperature under a nitrogen atmosphere for 3 hours. The reaction mixture was then quenched with 8 mL of 5% sodium hydroxide solution. The toluene layer was separated out, and the aqueous layer was extracted with ether (2×10 mL). The combined organic layers were dried over anhydrous sodium sulfate and then evaporated in vacuo. The residue obtained by evaporation was dissolved in 2 mL of ether, and then a saturated ethanolic solution containing 95 mg of fumaric acid was added to give on standing the fumarate salt of (3aS)-N$^1$-noresermethole (X): mp 199°–200° C. [α]$_D$–73.0° (c=0.7, MeOH). The product and a standard sample were identical when analyzed using a TLC plate (silica gel, CH$_2$Cl$_2$ with 5% MeOH).

EXAMPLE 4

0.9 g (2.7 mmol) of the fumarate salt of compound (X) prepared as in Example 3, was dissolved in 15 mL of methanol and 0.9 mL of triethylamine, with 1.35 mL of 37% formaldehyde solution being added thereto. The mixture was stirred at ambient temperature under a nitrogen atmosphere for 3 hours. The reaction mixture was then cooled to 0° C., and 0.41 g of sodium borohydride was added slowly in small portions. The mixture was stirred for another 0.5 hour. After the evaporation of solvent, the residue was dissolved in 15 mL of 1N HCl and washed with ether (10 mL), made basic by 10% NaHCO$_3$, and extracted with ether (3×20 mL). The combined ether layers were dried over Na$_2$SO$_4$ and evaporated in vacuo. The residue was passed through a short silica gel column to obtain 0.555 mg of (3aS)-esermethole (II) in 89% yield as a colorless oil: [α]$_D$–88.0° (c=1.2, CHCl$_3$). The product and a standard sample were identical when analyzed using a TLC plate (silica gel, CH$_2$Cl$_2$ with 5% MeOH).

EXAMPLE 5

An aqueous solution of the fumarate salt of compound (X) was treated with a 10% NaHCO$_3$ solution, and the free base was extracted with ether, and the ether solution was evaporated to obtain the free base. The free base was then dissolved in 30 mL of CH$_3$CN and 50 mg of dry K$_2$CO$_3$ and 2 g of benzylbromide were added. The reaction mixture was stirred at ambient temperature for 1 hour. After evaporation of solvent, the residue was chromatographed through a short silica gel column to obtain 1.3 g of the (3aS)-N$^1$-benzylnoresermethole (XI), in 70% yield as an oil: [α]$_D$–51.4° (c=1.5, CHCl$_3$). The product was identical with a standard sample when analyzed using a TLC plate (silica gel, CH$_2$Cl$_2$ with 1% MeOH).

EXAMPLE 6

528 mg of 1,3-dimethyl-3-carboxymethylmethyl-5-methoxyoxindole (XII) were heated with 8 mL of a 30% methylamine aqueous solution in a sealed tube in an oil bath held at 100° C. for 24 h. After the reaction mixture was cooled to room temperature, 80 mL of 2N HCl was added and the mixture was extracted with CH$_2$Cl$_2$ (3×80 mL). The combined extracts were washed with brine (100 mL), dried over Na$_2$SO$_4$, and evaporated in vacuo. The residue was passed through a short silica gel column to obtain 440 mg of 1,3-dimethyl-3-methylamidomethyl-5-methoxyoxindole (XIII) in 84% yield as crystals, mp 148°–149° C. The product and a standard sample were identical when analyzed using a TLC plate (silica gel, CH$_2$Cl$_2$ with 5% MeOH).

EXAMPLE 7

528 mg of 1,3-dimethyl-3-carboxymethylmethyl-5-methoxyoxindole (XII) were dissolved in 4 mL of MeOH, and 8 mL of benzylamine was added thereto. The reaction mixture was refluxed under nitrogen for 24 hours. The mixture was cooled to room temperature, and 100 mL of 2N HCl was added. The mixture was then extracted with CH$_2$Cl$_2$ (3×80 mL). The combined extracts were washed with brine (30 mL), dried over Na$_2$SO$_4$, and evaporated in vacuo. The residue was passed through a short silica gel column to obtain 600 mg of 1,3-dimethyl-3-benzylamidomethyl-5-methoxyoxindole (XIV) in 89% yield as crystals, m.p. 104°–105° C. The product and a standard sample were identical on a TLC plate (silica gel, CH$_2$Cl$_2$ with 5% MeOH).

EXAMPLE 8

170 mg of the amide (XIII) described in Example 6 was separated on the same column and under the same conditions as in Example 1 to obtain 80 mg of the first eluted 3aS enantiomer in 47% yield as a colorless gum: [α]$_D$+35.8.0° (c=1.03, CHCl$_3$), 10 mg of the mixture as colorless gum, and 80 mg of the 3aR enantiomer in 47% yield as colorless gum: [α]$_D$–37.5° (c=0.95, CHCl$_3$). An analysis of all three products on a TLC plate (silica gel, CH$_2$Cl$_2$ with 2% MeOH) indicated that the products were identical.

EXAMPLE 9

300 mg of the amide (XIV) described in Example 7 was separated on the same column and under the same conditions as in Example 1 to obtain 147 mg of the first eluted 3aR enantiomer in 49% yield as a colorless gum: [α]$_D$–64.2° (c=0.66, CHCl$_3$), 2.3 mg of the mixture as a colorless crystal, m.p. 104°–105° C. and 145 mg of the 3aS enantiomer in 49% yield as colorless crystal, m.p. 104°–105° C.: [α]$_D$+63.1° (c=0.77, CHCl$_3$). An analysis of all three products using a TLC plate (silica gel, CH$_2$Cl$_2$ with 2% MeOH) indicated that the products were identical.

EXAMPLE 10

The 3aS enantiomer of the amide (XIII) prepared as in Example 8 was reduced using Vitride in the manner set forth in Example 3 to obtain the (3aS)-esermethole (II) in 56% yield. The product and a standard sample were identical on a TLC plate (silica gel, CH$_2$Cl$_2$ with 5% MeOH).

EXAMPLE 11

The 3aS enantiomer of the amide (XIV) prepared as described in Example 9 was reduced using Vitride in the manner set forth in Example 3 to obtain the (3aS)-N$^1$-benzylnoresermethole (XI) in 56% yield. The product and a standard sample were identical on a TLC plate (silica gel, CH$_2$Cl$_2$ with 1% MeOH).

All of the references cited herein, including patents, and publications, are hereby incorporated in their entireties by reference.

While this invention has been described with an emphasis upon preferred embodiments, it will be obvious to those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

What is claimed is:

1. A method of separating a racemic mixture or a mixture enriched with one or other enantiomer, said mixture comprising the enantiomers of the compound of the formula:

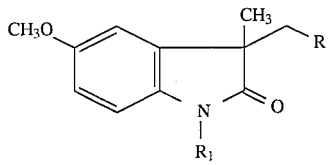

wherein R is CN or CONHR' where R' is selected from the group consisting of a $C_1$–$C_6$ alkyl, hydrogen, and benzyl, and $R_1$ is selected from the group consisting of $C_1$–$C_6$ alkyl and benzyl, said method comprising contacting said mixture with a cellulosic solid phase material comprising microcrystalline cellulose triacetate, eluting said mixture in contact with said material with an eluant, and recovering an eluted product having an enantiomeric excess greater than that of said mixture.

2. The method of claim 1, wherein R is CN, $CONH_2$, $CONHCH_2C_6H_5$, or $CONHCH_3$, and $R_1$ is $CH_3$.

3. The method of claim 2, wherein the enantiomeric excess of said eluted product is at least about 80%.

4. The method of claim 3, wherein the enantiomeric excess of said eluted product is about 100%.

5. The method of claim 4, wherein the enantiomeric excess of said mixture enriched with one or other enantiomer is about 60–80%.

6. The method of claim 2, wherein said eluant comprises alcohol selected from the group consisting of methanol, ethanol, propanol, isopropanol, n-butanol, sec-butanol, and t-butanol, and combinations thereof.

7. The method of claim 6, wherein said alcohol is ethanol.

8. The method of claim 7, wherein said eluant further comprises water.

9. The method of claim 8, wherein said eluant comprises at least about 90 vol. % of said alcohol.

10. A method of separating a racemic mixture or a mixture enriched with one or other enantiomer, said mixture comprising the enantiomers of the compound of the formula:

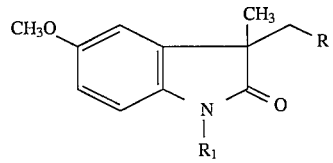

wherein R is CONHR' where R' is selected from the group consisting of a $C_1$–$C_6$ alkyl, hydrogen, and benzyl, and $R_1$ is selected from the group consisting of $C_1$–$C_6$ alkyl and benzyl, said method comprising contacting said mixture with a cellulosic solid phase material, eluting said mixture in contact with said material with an eluant, and recovering an eluted product having an enantiomeric excess greater than that of said mixture.

11. The method of claim 10, wherein the enantiomeric excess of said eluted product is at least about 80%.

12. The method of claim 11, wherein the enantiomeric excess of said mixture enriched with one or other enantiomer is about 60–80%.

13. The method of claim 10, wherein said cellulosic solid phase material is selected from the group consisting of microcrystalline cellulose triacetate, cellulose diacetate, cellulose p-methylbenzoate, and 3,5-dimethylphenylcarbamate cellulose, and combinations thereof.

14. The method of claim 13, wherein said cellulosic solid phase material is microcrystalline cellulose triacetate.

15. The method of claim 10, wherein said eluant is an alcohol.

16. The method of claim 15, wherein said alcohol is selected from the group consisting of methanol, ethanol, propanol, isopropanol, n-butanol, sec-butanol, and t-butanol, and combinations thereof.

17. The method of claim 10, wherein the cellulosic solid phase material is microcrystalline cellulose triacetate and the eluant comprises ethanol.

18. The method of claim 17, wherein said eluant further comprises water.

19. The method of claim 18, wherein said eluant comprises at least about 90 vol. % of said ethanol.

20. A method of separating a racemic mixture or a mixture enriched with one or other enantiomer, said mixture comprising the enantiomers of the compound of the formula:

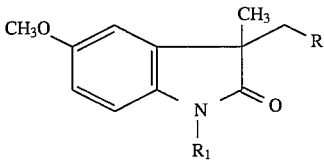

wherein R is CN, and $R_1$ is $C_1$–$C_6$ alkyl, hydrogen, or benzyl, said method comprising contacting said mixture with a cellulosic solid phase material, eluting said mixture in contact with said solid phase material with an eluant that is substantially free of hexane, and recovering an eluted product having an enantiomeric excess greater than that of said mixture.

21. The method of claim 20, wherein the enantiomeric excess of said eluted product is at least about 80%.

22. The method of claim 21, wherein the enantiomeric excess of said eluted product is about 100%.

23. The method of claim 22, wherein the enantiomeric excess of said mixture enriched with one or other enantiomer is about 60–80%.

24. The method of claim 20, wherein said cellulosic solid phase material is selected from the group consisting of microcrystalline cellulose triacetate, cellulose diacetate, cellulose p-methylbenzoate, and 3,5-dimethylphenylcarbamate cellulose, and combinations thereof.

25. The method of claim 24, wherein said cellulosic solid phase material is microcrystalline cellulose triacetate.

26. The method of claim 24, wherein said alcohol is selected from the group consisting of methanol, ethanol, propanol, isopropanol, n-butanol, sec-butanol, and t-butanol, and combinations thereof.

27. The method of claim 20, wherein the cellulosic solid phase material is microcrystalline cellulose triacetate and said alcohol is ethanol.

28. The method of claim 27, wherein said eluant further comprises water.

29. The method of claim 28, wherein said eluant comprises at least about 90 vol. % of said alcohol.

* * * * *